United States Patent
Watanabe (10) Patent No.: US 8,297,280 B2
(45) Date of Patent: Oct. 30, 2012

(54) INHALER

(75) Inventor: Shinji Watanabe, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 1015 days.

(21) Appl. No.: 12/167,362

(22) Filed: Jul. 3, 2008

(65) Prior Publication Data

US 2009/0020113 A1    Jan. 22, 2009

(30) Foreign Application Priority Data

Jul. 20, 2007    (JP) .................................. 2007-189203

(51) Int. Cl.
*F16K 31/26* (2006.01)
(52) U.S. Cl. ......... 128/204.23; 128/200.24; 128/200.14; 128/200.23; 128/204.18; 128/204.21
(58) Field of Classification Search ............. 128/200.14, 128/200.23, 204.18, 204.21, 204.23
See application file for complete search history.

(56) References Cited

U.S. PATENT DOCUMENTS

| 5,363,842 A | * | 11/1994 | Mishelevich et al. .... 128/200.14 |
| 5,608,647 A | | 3/1997 | Rubsamen et al. ........... 700/281 |
| 5,655,516 A | * | 8/1997 | Goodman et al. ....... 128/200.14 |

FOREIGN PATENT DOCUMENTS

| WO | WO 95/01137 A1 | 1/1995 |
| WO | WO 00/53247 | 9/2000 |
| WO | WO 01/58514 | 8/2001 |
| WO | WO 02/04043 A2 | 1/2002 |

* cited by examiner

*Primary Examiner* — Lynne Anderson
*Assistant Examiner* — Bradley Philips
(74) *Attorney, Agent, or Firm* — Fitzpatrick, Cella, Harper & Scinto (57) ABSTRACT

An object of the present invention is to enhance the inhalation efficiency by causing liquid droplets to be borne on an air flow in an early stage of inhalation in an inhaler. According to one embodiment, from an operation in which the user lets out a breath before the start of inhalation (that is, from exhalation), a positive pressure B produced by the exhalation is detected by a pressure detecting unit, and is compared with a standard pattern stored in a storage unit, and in this way the exhalation profile of the user is prepared. A time difference t between the exhalation finish time and the start time of the next inhalation is estimated, followed by the determination of the ejection start time T1 based on these pieces of information.

9 Claims, 6 Drawing Sheets

INHALER

BACKGROUND OF THE INVENTION

1. Field of the Invention

The present invention relates to an inhaler that is configured so as to be carried with the user and is used to effect efficient administration of a medicine for health care by ejecting and inhaling the medicine as minute liquid droplets.

2. Description of the Related Art

In recent years, average life span has lengthened due to progress in medical science and natural science, and an aging society is one result. On the other hand, people's anxiety about health has increased because of changes in eating habits and living environment, an increase in environmental pollution, and discovery of new diseases and infectious diseases caused by viruses and bacteria. Especially in the developed countries, the increase in patients with lifestyle-related diseases such as diabetes mellitus and hypertension has posed a problem.

On the other hand, the number of medical institutions has not increased in step with the increase in such patients, and some regions have no medical institution to which patients can go regularly.

Hereunder, description will be given by taking a specific example. Among patients with diabetes mellitus, the prevalence of which is increasing at present, patients with insulin-dependent diabetes mellitus (called "type I") must take insulin periodically because insulin is not secreted by their pancreas. Since the insulin is administered by hypodermic injection at present, the user's physical and psychological burdens are heavy.

To reduce such user's burdens, a pen-type syringe that has a thin needle and scarcely gives pain has been developed. However, patients with type-I diabetes mellitus often lead the same life as that of healthy persons except for the need to self-administer insulin periodically. Therefore, even with a syringe of pen type, patients are psychological reluctant to given themselves an injection in the presence of other people, so that it is difficult to administer insulin at the proper time. As a result, such a method has a possibility that proper treatment of the user is not performed.

Also, chronic obstructive pulmonary disease (COPD) that seems to appear from chronic inflammation of the lungs due to smoking, etc., is also a lifestyle-related disease of the lungs that has received attention recently. In this disease, early symptoms are slight and difficult to notice, so that pulmonary function declines with age, which finally leads to chronic respiratory insufficiency and deterioration in the patient's general condition, hindering daily life. In many cases, the conventional treatment of COPD is performed by inhaling a medicine having bronchial tube expanding action by using a metered dose inhaler ("MDI") or a dry powder inhaler ("DPI").

A medicine ejection apparatus by means of which the user can take a medicine by inhalation, and which can make the most of an information database such as an electronic medical chart, is known for treatment of a patient. Such a medicine ejection apparatus has a storage unit for storing information about the individual user, including information of the user's medical chart and medical prescription. Such a medicine ejection apparatus, which is also a portable terminal that is also used as a medicine inhaler in which a medicine is ejected as minute droplets and is inhaled by the user, has a control section for controlling the inhaler to eject the medicine.

The medicine ejection apparatus as described above can exactly control the dosage of medicine according to the medical prescription. According to this, unlike the conventional medicine administration, a medical instrument such as a syringe need not be used at the time of medicine administration. Therefore, the operation can be performed easily without expert knowledge, and also the user is spared the pain caused by use of a needle.

Also, it is generally known that the intrapulmonary deposition of minute droplets of medicine caused by inhalation depends on the particle diameter of the medicine. For example, transmission to the vicinity of bronchial tube requires a particle-size distribution of about 7 µm of medicine diameter, and transmission to the pulmonary alveoli, which are deep in the lung, requires a narrow particle-size distribution of about 3 µm of medicine diameter. By applying inkjet technology, which has been fostered by development of printers performing highly fine printing, especially the thermal inkjet technology, to the ejection of medicine, a liquid medicine can be turned to minute liquid droplets having a narrow particle-size distribution. By this technology, more efficient medicine taking or more proper medicine transmission to a diseased part than conventional treatment can be realized (refer to International Publications WO95/01137 and WO02/04043).

Conventionally, at the time of medicine inhalation, the user's action for taking a breath, that is, the negative pressure produced in an air flow path by the inhalation, is detected by a pressure detecting unit, and the ejection is started in association with the output of the pressure detecting unit. At this time, if the medicine is ejected at the moment when the pressure detecting unit detects the negative pressure, the medicine is ejected if there is a temporary and minute pressure change produced by a change in usage environment rather than by the user's inhalation, and thus the medicine may be wasted. Such ejection is unfavorable in terms of hygiene as well. Therefore, generally, if the negative pressure in the air flow path exceeds a fixed value, it is determined that the pressure change is produced by the user's inhalation, and only then is the ejection of medicine started. That is to say, in order to start the ejection, the elapse of a predetermined time has been needed from the time when the inhalation has begun. Also, depending on the user's manner of inhalation, the time until the pressure reaches a pressure level at which it can be determined that the inhalation has been performed differs from person to person.

On the other hand, when medication is accomplished through the lungs, in order to absorb the medicine from the pulmonary alveoli into the human body most efficiently, it seems desirable that the medicine arrives at the farthest (deepest) part in the lungs. For this purpose, as is well known, it is ideal that the liquid droplets are borne on the air flow early during the time of inhalation. However, in the method in which the ejection is started after the predetermined negative pressure has been detected as described above, it is difficult to bear liquid droplets on the air flow early during the time of inhalation.

SUMMARY OF THE INVENTION

The present invention has been made to solve the above problems, and accordingly an object thereof is to provide an inhaler capable of bearing an ejected medicine on the early part of the inhalation of the user more quickly and surely as compared with the conventional inhaler.

To achieve the above object, the present invention provides an inhaler including: an ejection unit for ejecting a medicine which is inhaled by a user; an air flow path for guiding the medicine, which has been ejected from the ejection unit, to a suction port; a detecting unit for detecting the exhalation of the user through the suction port in a space in the air flow path or a space communicating therewith; an estimating unit for estimating a time difference between exhalation finish and inhalation start of the user; and a control unit for controlling the drive of the ejection unit, where the control unit starts the drive of the ejection unit based on the exhalation finish time determined by the output from the detecting unit and the time difference estimated by the estimating unit.

By virtue of the configuration described above, advantages described below are achieved. An operation in which the user lets out a breath before the start of inhalation, that is, an exhalation operation, is detected, and the finish time of the exhalation can be determined. Also, the start time (timing) of the next inhalation can be predicted. Based on these pieces of information, more efficient inhalation as compared with the conventional inhaler can be accomplished by the start of ejection.

When a medicine is inhaled by the spontaneous breathing of the user, the medicine can be borne on the early part of inhalation by predicting the inhalation start at the time of inhalation operation of the user and by controlling the ejection unit based on the prediction without the use of an external measuring instrument.

A long-term breathing pattern need not be observed, and the user is not restricted. Also, since ejection is accomplished after the exhalation finish, the medicine is not wasted, and the inhalation efficiency is enhanced.

Other features and advantages of the present invention will be apparent from the following description taken in conjunction with the accompanying drawings, in which like reference characters designate the same or similar parts throughout the figures thereof.

DESCRIPTION OF THE EMBODIMENTS

Preferred embodiments of the present invention will now be described in detail in accordance with the accompanying drawings.

Embodiment 1

Figure 1:
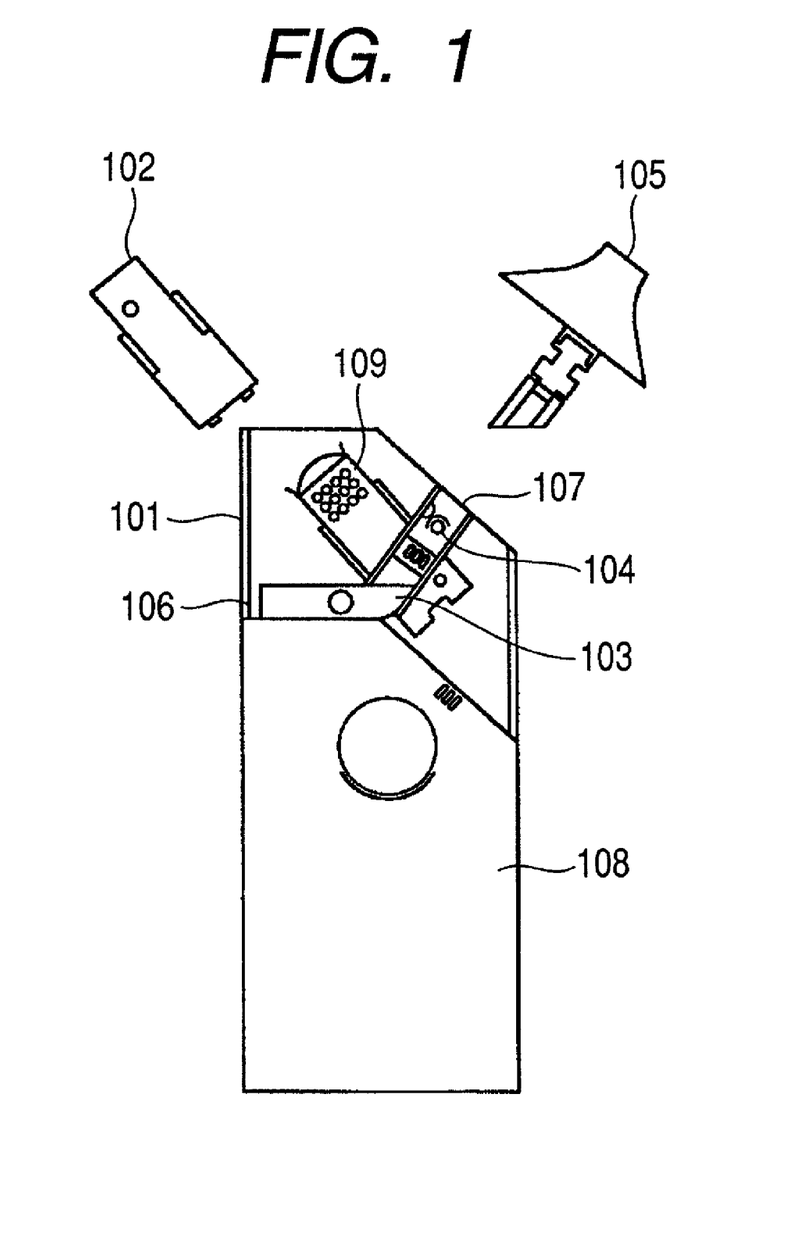
FIG. 1 is an exploded view illustrating a configuration of an inhaler according to Embodiment 1.
Figure 2:
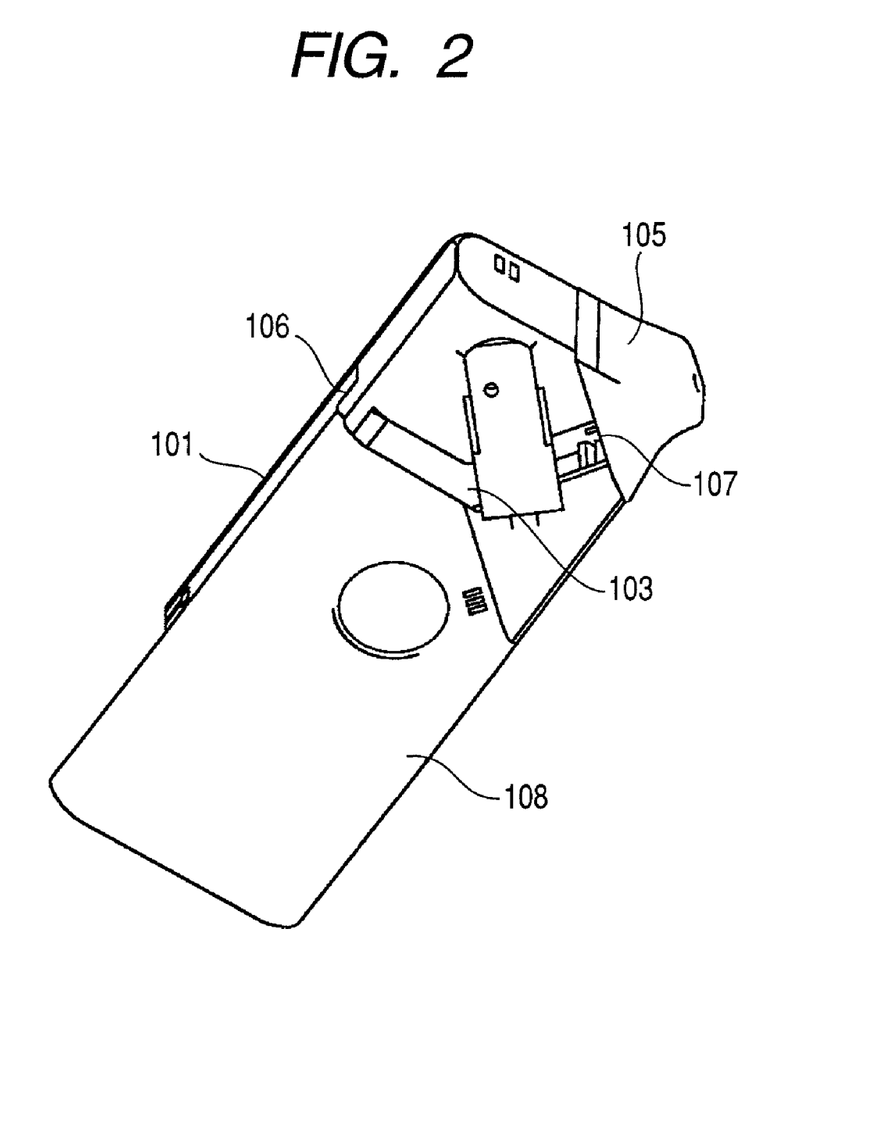
FIG. 2 is a perspective view illustrating an appearance of the inhaler illustrated in FIG. 1.

FIGS. 1 and 2 illustrate a principal part of an inhaler of Embodiment 1. This inhaler has an inhaler body 101 and a medicine cartridge 102. The medicine cartridge 102 includes an ejection head, which is an ejection unit for ejecting a medicine that is inhaled by the user, and a reservoir that stores the medicine. The ejection head can have a configuration in which liquid droplets having a narrow particle-size distribution between 1 and 5 μm of liquid droplet diameter can be ejected. For example, the ejection head can have a configuration having an electrothermal transducer that gives thermal energy to the medicine (thermal inkjet system) or an electromechanical transducer that gives mechanical energy to the medicine (piezo-inkjet system). In the case where the thermal inkjet system is used, for an individual head, the diameter of ejection port, the heating value of thermal pulse used for ejection, the size accuracy of the micro-heater used for the thermal pulse, and the reproducibility can be increased. Therefore, a narrow liquid droplet diameter distribution can be attained. Also, the manufacturing cost of the head is low, and the applicability to a small-sized inhaler in which the head must be exchanged frequently is also high. Therefore, in the case where the inhaler requires portability or convenience, the thermal inkjet system is especially favorable.

The medicine cartridge 102 is detachably attached to a cartridge attachment part provided on the inhaler body 101. Also, when the medicine cartridge 102 is attached to the cartridge attachment part, the electric connection part thereof connects with an electric contact 109 in the cartridge attachment part, by which electric power and various control signals are supplied from the battery and control circuit on the inhaler body side. A CPU, which is a control unit for controlling the drive of ejection head, is also provided on the inhaler body side. Therefore, the drive control of ejection head can be carried out by the above-described electrical contacting.

An air flow path 103 provided in the inhaler body 101 guides the medicine, which is ejected from the ejection head, to a mouthpiece 105 that serves as a suction port. In FIGS. 1 and 2, the air flow path 103 is formed so as to be curved because of the arrangement relation with other components. However, the air flow path 103 may be formed so as to extend straight. When the medicine cartridge 102 is attached to the cartridge attachment part, the ejection port surface of ejection head is exposed to the air flow path 103. In the space in the air flow path 103, a pressure detecting unit (pressure sensor) 104, which is a detecting unit for detecting the fluctuations in pressure, is arranged. The pressure sensor itself may be provided in a space communicating with the air flow path 103. For the mouthpiece 105, which is used when the user inhales a liquid medicine, the concave part thereof engages with a convex part provided in the air flow path 103, by which the mouthpiece 105 can be detachably attached to the inhaler body 101. It is desirable that the medicine cartridge 102 and the mouthpiece 105 be used only once and then thrown away or exchanged periodically, from the viewpoint of hygiene, so that a construction in which the medicine cartridge 102 and the mouthpiece 105 are integrated rather than detachable may be used.

In the description below, the pressure detecting unit 104 is used as a detecting unit for detecting the exhalation and inhalation of the user. However, the pressure detecting unit is not limited to this. As a unit for detecting the exhalation and inhalation of the user, for example, a flowmeter that measures air flow produced by the breathing of the user can also be thought of.

The air flow path 103 is provided with an inlet (air inlet port) 106 at one end and an outlet (discharge port) 107. When the mouthpiece 105 is mounted on the outlet 107 and the operation button is pushed, a state is formed in which a medicine can be ejected from the ejection head of the medicine cartridge 102. Air is introduced from the inlet 106 by the inhaling operation, and the medicine ejected into the air flow path is taken into the human body through the mouthpiece 105 attached to the outlet 107.

When an air flow is produced in the air flow path 103 by the exhalation or inhalation of the user, the pressure detecting unit 104 detects a negative pressure or a positive pressure as an electric signal.

Further, a slide-type cover 108 is arranged. By slidingly closing the cover 108, the open part of the air flow path 103 is closed, and the medicine cartridge 102 is fixed. FIGS. 1 and 2 show the opened state. The power switch may be operated in association with the closing of the cover 108.

Figure 3A:
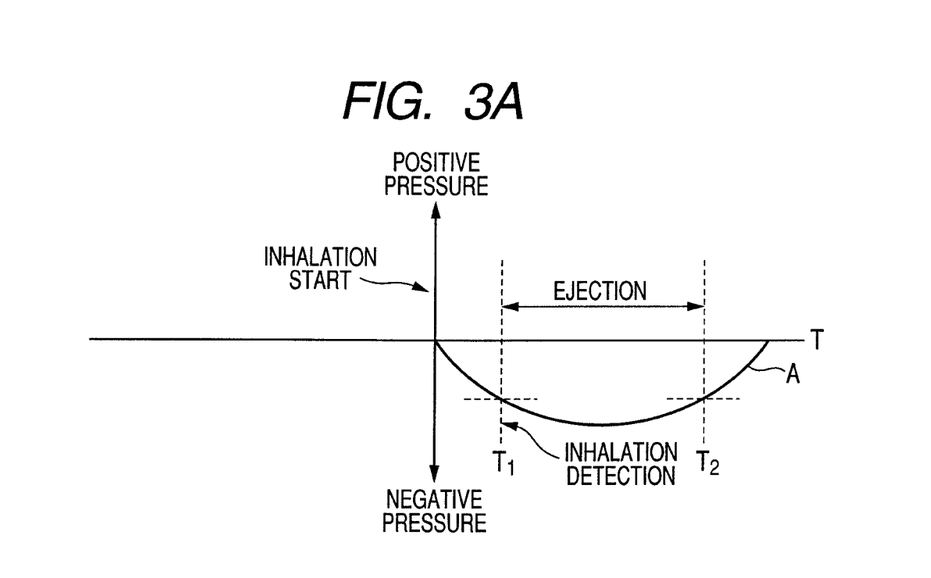
FIGS. 3A and 3B are graphs for describing the operation of the inhaler.

As illustrated in FIG. 3A, in the conventional inhaler, the negative pressure A produced in the air flow path by the inhalation action is detected by the pressure detecting unit, and when a predetermined negative pressure is reached, ejection is first started in association with the output thereof. That is to say, at the time T1 of ejection start, the elapse of predetermined time from when inhalation is started is indispensable. Usually, the produced negative pressure can be detected from the inhalation start by the pressure detecting unit. However, to distinguish an erroneous output caused by disturbance such as wind or vibrations from a normal output caused by inhalation or to check that the output is an attraction force capable of reaching the lungs, waiting time must be provided until a detection level of some degree is reached. Therefore, depending on the manner of inhalation of the user as well, the time before the detection level is reached differs. That is to say, an uncertain difference in time is produced from when inhalation is started to when ejection is started.

Also, at the final stage of inhalation, the inhaled air does not reach the lungs when the attraction amount is smaller than the dead space volume from the oral cavity to the respiratory tract, and is discharged to the outside of the human body as it is. Therefore, when the output of the pressure detecting unit is lower than a certain detection level and the final stage of inhalation is detected (time T2), the ejection is inevitably finished. For this reason, the effective period for which ejection is enabled is uncertain.

Figure 3B:
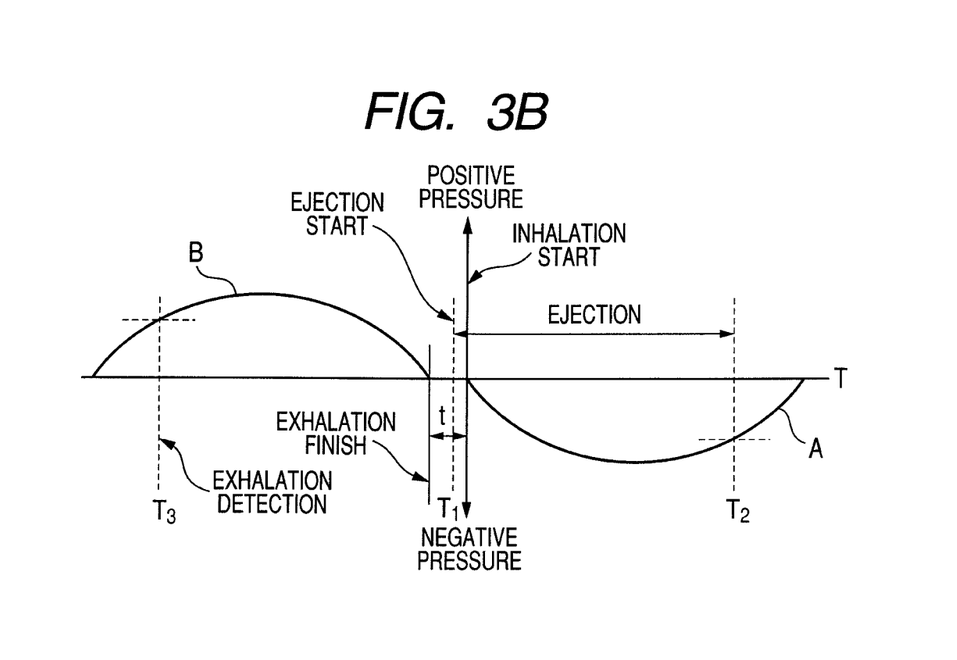

Accordingly, in the present invention, as illustrated in FIG. 3B, before the user inhales a liquid medicine, the user holds the mouthpiece in his/her mouth and lets out a breath. The positive pressure B produced in the air flow path by this exhalation is detected by the pressure detecting unit. Like the conventional inhalation detection, the detection of exhalation start may be started from the time T3 when the output of pressure detecting unit reaches a certain level to prevent erroneous detection. The positive pressure B produced by exhalation as well, like the negative pressure A, reaches the peak from the detection of the exhalation start and lowers toward the end of exhalation. By recording this data, the inhaler can detect the time of exhalation finish. That is to say, the time when the pressure becomes zero after the pressure sensor has generated an output signal telling that a positive pressure is detected can be determined as the exhalation finish time.

To prevent the waste of medicine, the ejection must be started at a time at which exhalation is finished and air flow that discharges air to the outside of the air flow path is stopped. After the exhalation has finished, the user starts continuous inhalation. Usually, there is a time difference t during which exhalation turns to inhalation. It can be thought that this time difference t may have an individual difference depending on sex, physical constitution, age, or the state of disease (in a case where the user has a respiratory disease). Therefore, the time difference t estimated based on the individual data of the user is stored in advance in the storage unit in the inhaler body as a table. By referring to this table, the timing of inhalation start can be determined by an arithmetic unit. In this embodiment, this table functions as an estimating unit. Based on the exhalation finish time determined by the output from the pressure sensor and the information of time difference t recorded as the table, the control unit starts driving of the ejection head, thereby starting the ejection of medicine. Thereby, the liquid droplets are borne on the air flow at the early stage of inhalation, by which the liquid medicine can be administered more efficiently.

As described above, to prevent the waste of liquid medicine, the ejection must be started in the state in which the exhalation is finished and the air flow that discharges air outside the air flow path is stopped. Similarly, at the final stage of inhalation, the inhaled air does not reach the lungs when the remaining attraction amount is smaller than the dead space volume from the oral cavity to the respiratory tract, and is discharged outside the body as it is. However, if the condition that exhalation is finished and more inhaled air than the dead space volume can be attracted is met, the time T1 of ejection start can be determined arbitrarily.

In the case where the inhaler is used especially for the treatment of pulmonary disease and for the treatment of the lungs themselves, a need for causing the liquid medicine to arrive at the diseased part arises. By improving the time difference t between exhalation finish and inhalation start and the prediction accuracy of the inhalation profile, the liquid medicine is borne on the air flow at the early stage of inhalation. Thereby, not only can the liquid medicine be administered more efficiently, but also the accuracy of liquid medicine arrival part can be improved. That is to say, the ejection can be started at arbitrary timing from the time before inhalation start to the time after inhalation start according to the necessary administering method.

In the present invention, since the objective is to start the ejection at an earlier stage of inhalation than the conventional treatment, the ejection start is estimated by the above-described process, and is not limited to the determined inhalation start time. However, it is unfavorable to start the ejection before the exhalation of the user finishes.

From the above-described viewpoint, the favorable timing for the control unit to start driving of ejection unit in the present invention is described below. First, the control unit can start driving of the ejection unit from when the exhalation determined by the output from the detecting unit to when a predetermined period of time has elapsed from inhalation start by the user. The predetermined period of time is T1 in FIG. 3A, that is, the time until the negative pressure reaches a threshold value at which the pressure sensor can determine the inhalation of the user. By doing this, the ejection of medicine can be started at an earlier timing than in the case where only inhalation is detected. Also, the control unit can further start driving of the ejection unit from when the exhalation determined by the output from the detecting unit to when the inhalation of the user is started. The same is true for the embodiments described below.

Embodiment 2

Figure 4:
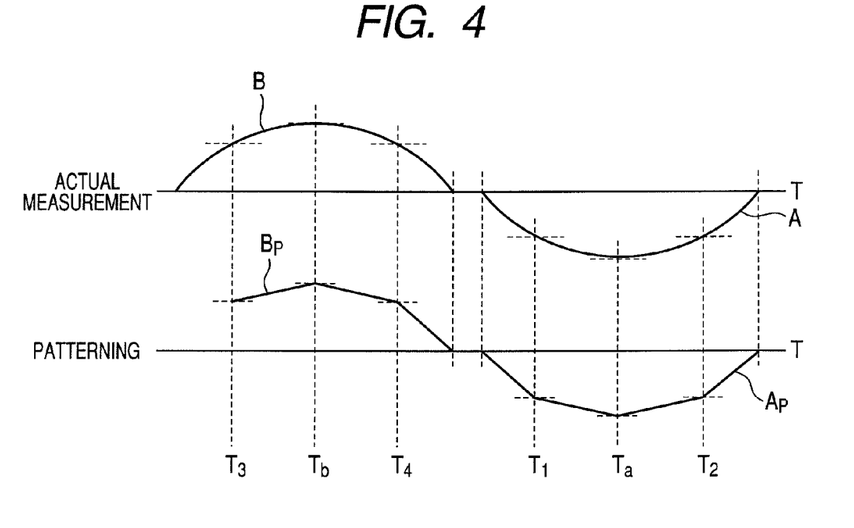
FIG. 4 is a graph illustrating a method for patterning a positive pressure and a negative pressure produced by exhalation and inhalation.

Embodiment 2 has the same inhaler configuration as that of Embodiment 1. In the inhaler of Embodiment 2, as illustrated in FIG. 3A, the positive pressure A and the negative pressure B produced by breathing are measured, and can be recorded as a profile such as exhalation intensity, duration, and the like. This profile need not record all pressure waveforms. For example, as illustrated in FIG. 4, the positive pressure A and the negative pressure B from the detection time T1, T3 to the maximum pressure time Ta, Tb, and the pressure decrease time T2, T4 may be recorded as patterned pressure data Ap, Bp.

Figure 5:
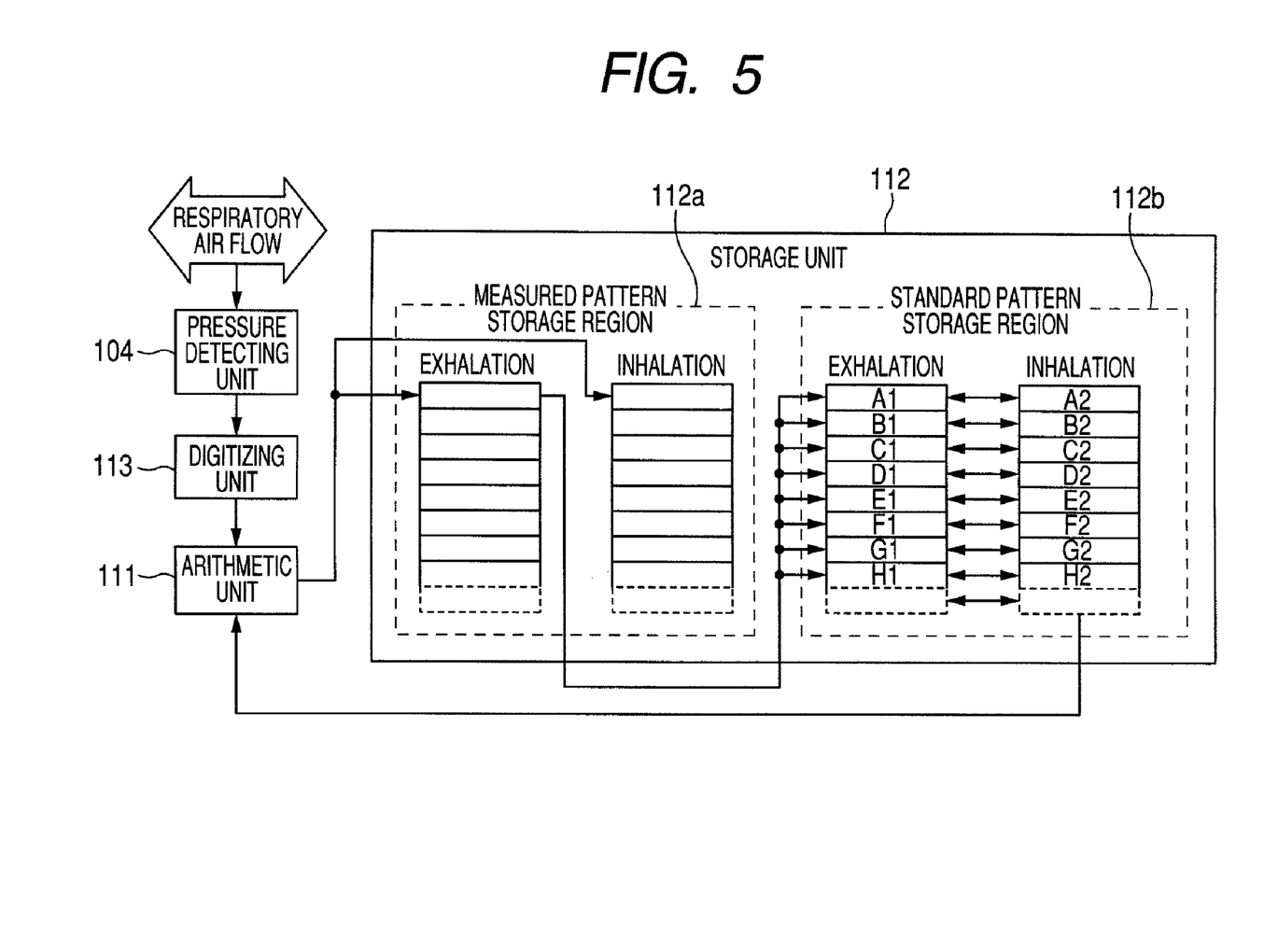
FIG. 5 is a block diagram illustrating a control section of an inhaler according to Embodiment 2.
Figure 6:
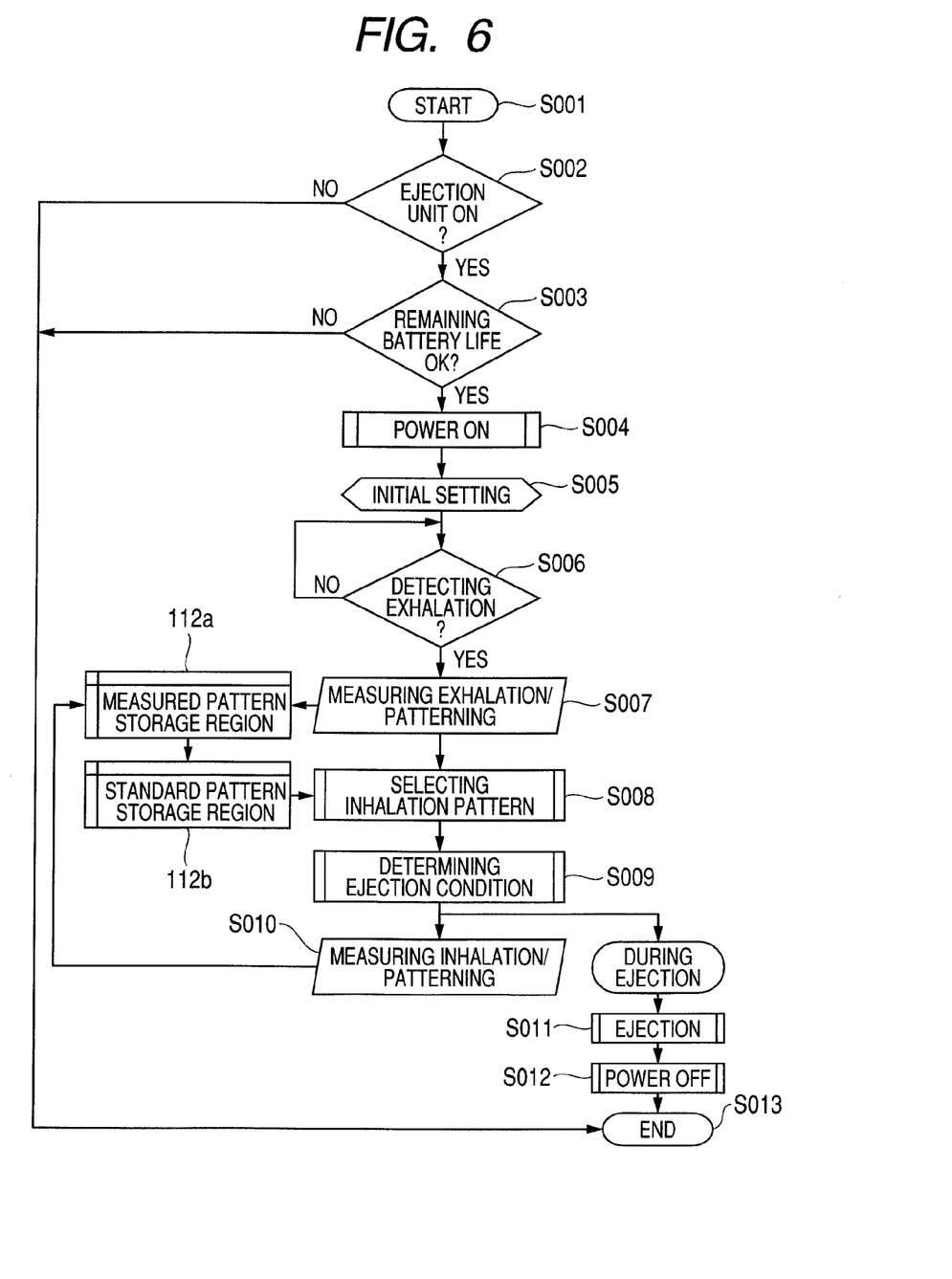
FIG. 6 is a flowchart illustrating the operation of an inhaler according to Embodiment 2.

FIG. 5 is a block diagram illustrating a control section of the inhaler of this embodiment, and FIG. 6 is a flowchart illustrating the operation of this embodiment. The control section illustrated in FIG. 5 has an arithmetic unit 111 and a storage unit (memory) 112, and is connected to the pressure detecting unit 104 via a digitizing unit 113 such as an A/D converter.

Next, the operation of the inhaler is described with reference to FIG. 6. After the operation start of the inhaler (S001), the medicine cartridge 102 is checked (S002), and the remaining battery life is checked (S003). If there is no problem, the power is turned on (S004), by which a state in which the user can use the inhaler is formed. In this state, the inhaler begins to detect the exhalation of the user (S005).

The exhalation just before the inhalation operation of liquid medicine is measured by the pressure detecting unit 104, and is patterned by the arithmetic unit 111 via the digitizing unit 113 (S006). The storage unit 112 has a measured pattern storage region 112a that stores the measured data of exhalation and the measured data of inhalation. Also, the storage unit 112 has a standard pattern storage region 112b that stores the standard exhalation pattern corresponding to the individual data including sex, physical constitution, age, and the state of disease of the user and the inhalation pattern including the time difference corresponding to the individual data. The measured and patterned exhalation profile is recorded in the measured pattern storage region 112a of the storage unit 112. This measured pattern is compared with the standard exhalation pattern recorded in the standard pattern storage region 112b. Since the standard exhalation pattern corresponds to the individual data including sex, physical constitution, age, and the state of disease, if the measured exhalation pattern does not fit the standard exhalation pattern, an alarm is given to the user as an abnormal value (S007). If it is determined that the measured exhalation pattern is normal, a similar standard exhalation pattern can be selected. At the same time, the standard exhalation pattern stores the corresponding time difference and standard inhalation pattern, so that the time difference and standard inhalation pattern having the highest probability at the time when the exhalation is measured can be selected (S008).

Based on the selected standard inhalation pattern, ejection parameters such as the time of ejection start, the ejection frequency, the ejection time, and the driving voltage are determined (S009), and the ejection is started (S010).

In this embodiment, based on the individual data and the measured exhalation profile, the time difference between the exhalation finish and the inhalation start of the user is determined. Since the exhalation is detected, and the time of exhalation finish can be determined, this information is combined to calculate the time of inhalation start. The fact that the ejection is started based on the calculated time of inhalation start is the same as that in Embodiment 1. During the ejection operation, like the measurement and patterning of exhalation, the inhalation profile is also measured and patterned in parallel, and can be recorded in the storage unit 112. After the ejection has been finished, the power is turned off (S011), by which the operation is finished (S012).

In the conventional method, in which only inhalation is monitored, and ejection is accomplished only during the time when a fixed negative pressure is produced, the duration of inhalation cannot be predicted, and the ejection parameter is fixed. In this case, since ejection is accomplished with a fixed ejection parameter, one inhalation operation is often insufficient for a necessary dosage, so that there is a possibility that a need for performing inhalation a plurality of times may arise. Alternatively, in order to secure the necessary dosage in a short period of time, in some cases, a load is imposed on the medicine cartridge 102 by accomplishing ejection with high frequency and high energy.

In this embodiment, since ejection can be started by predicting the inhalation start, first, the period of time during which the ejection can be accomplished can be lengthened as compared with the conventional method. Further, since the inhalation profile including the intensity and duration of inhalation just after the ejection is predicted from the exhalation profile, the ejection parameters such as the ejection frequency, the ejection time, and the driving voltage can be changed so that a necessary dosage is secured by one inhalation operation. That is to say, the ejection can be accomplished in large quantities or while lightening the load of the medicine cartridge 102 as compared with the conventional ejecting method.

Embodiment 3

In an inhaler having the same configuration as that of Embodiment 2, during the ejection using the medicine cartridge 102, the inhalation profile including the aforementioned time difference is also measured and patterned by the pressure detecting unit 104, and is recorded in the storage unit 112 as an exhalation/inhalation profile. Since exhalation and inhalation are accomplished as a series of operations, detection of negative pressure need not be based on the output reaching a certain level, unlike the start time of exhalation, and the profile can be acquired as a waveform continuing from positive pressure to negative pressure. Also, the profiles are classified for each exhalation pattern similar to the acquired data by referring to the past data, and are weighted by appearance frequency, and thus all waveforms need not be recorded each time the inhaler is used.

Since the accumulated pattern is a pattern of time difference and inhalation corresponding to the own exhalation of the user, by the repeated use, the time difference t is corrected by the method in which the standard value is revised by the measured value or the average of the measured value and the standard value is taken, and thereby the prediction accuracy can be improved.

Embodiment 4

In an inhaler similar to Embodiment 3, there is provided a control section having an operation mode that records an exhalation/inhalation profile (an exhalation profile and an inhalation profile) in the storage unit 112, and measures and records a series of exhalation and inhalation before the actual liquid medicine is inhaled. Based on the exhalation/inhalation profile measured in advance, the time difference between exhalation finish and inhalation start and the inhalation profile are determined. In this case, even if the individual data including sex, physical constitution, age, and the state of disease of the user is not input, the same effect can be achieved by the iterative operation of the user.

To realize this function, it is desirable to provide audiovisual and other display functions for telling the user whether the operation is of an operation mode for acquiring the exhalation/inhalation profile or of a liquid medicine inhalation mode. Also, since the exhalation/inhalation profile acquired in advance and the breathing profile at the time of liquid medicine inhalation are required to have high similarity, it is desirable that the modes be accomplished without an interval of time if possible. For this purpose, the configuration may be such that the operation mode for acquiring the exhalation/ inhalation profile and the liquid medicine inhalation mode are changed over automatically and continuously.

The present invention is not limited to the above embodiments and various changes and modifications can be made within the spirit and scope of the present invention. Therefore to apprise the public of the scope of the present invention, the following claims are made.

This application claims the benefit of Japanese Patent Application No. 2007-189203, filed Jul. 20, 2007, which is hereby incorporated by reference herein in its entirety.

The invention claimed is:

1. An inhaler comprising:
an ejection unit for ejecting a medicine which is inhaled by a user;
an air flow path for guiding the medicine, which has been ejected from said ejection unit, to a suction port;
a detecting unit for detecting exhalation and inhalation of the user through the suction port in a space in said air flow path or a space communicating therewith;
memorizing unit for memorizing a time difference between exhalation finish and inhalation start of the user; and
a control unit for controlling driving of said ejection unit, wherein said control unit starts driving of said ejection unit based on an exhalation finish time determined by an output from said detecting unit and the time difference memorized by said memorizing unit, and wherein, after starting driving of said ejection unit, a corrected time difference is determined based on exhalation and inhalation of the user detected by said detecting unit, and said memorizing unit memorizes the corrected time difference.

2. The inhaler according to claim 1, wherein said memorizing unit stores individual data of the user, and memorizes estimates the time difference between exhalation finish and inhalation start of the user based on the individual data.

3. The inhaler according to claim 2, wherein said memorizing unit stores an exhalation profile of the user based on the output from said detecting unit, and memorizes the time difference between exhalation finish and inhalation start of the user based on the individual data and the exhalation profile.

4. The inhaler according to claim 1, wherein said memorizing unit stores an exhalation profile of the user based on the output from said detecting unit, and predicts an inhalation profile from the exhalation profile.

5. The inhaler according to claim 1, wherein said detecting unit detects inhalation and exhalation of the user, exhalation/inhalation profile of the user based on the output from said detecting unit is stored, and the corrected time difference is determined.

6. The inhaler according to claim 1, wherein an operation mode is provided to acquire only an exhalation/inhalation profile of the user by using said detecting unit without ejection of a liquid medicine by said ejection unit, and
wherein said memorizing unit stores the exhalation/inhalation profile of the user acquired in the operation mode, and memorizes the time difference between exhalation finish and inhalation start of the user.

7. The inhaler according to claim 1, wherein said detecting unit is a pressure detecting unit for detecting pressure in said air flow path.

8. The inhaler according to claim 1, wherein said control unit starts driving of said ejection unit during a period of time from the exhalation finish time determined by the output from said detecting unit to until a predetermined time from a beginning of inhalation by the user.

9. The inhaler according to claim 1, wherein said control unit starts driving of said ejection unit during a period of time from the exhalation finish time determined by the output from said detecting unit to a beginning of inhalation by the user.

* * * * *